United States Patent
Macklis et al.

(12) 
(10) Patent No.: US 6,703,632 B1
(45) Date of Patent: Mar. 9, 2004

(54) RADIATION SHIELD

(75) Inventors: Roger M. Macklis, Cleveland, OH (US); Jason Sohn, Chesterfield, MO (US); Twyla Willoughby, Orlando, FL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/089,886

(22) PCT Filed: May 31, 2000

(86) PCT No.: PCT/US00/14974

§ 371 (c)(1),
(2), (4) Date: Oct. 17, 2002

(87) PCT Pub. No.: WO00/74072

PCT Pub. Date: Dec. 7, 2000

Related U.S. Application Data

(60) Provisional application No. 60/136,987, filed on Jun. 1, 1999.

(51) Int. Cl.[7] ................................................. G21F 3/00
(52) U.S. Cl. .................. 250/515.1; 250/519.1
(58) Field of Search ............................ 250/515.1, 519.1

(56) References Cited

U.S. PATENT DOCUMENTS

| | | | | |
|---|---|---|---|---|
| 4,158,779 A | * | 6/1979 | Rommel et al. | 250/515.1 |
| 5,190,990 A | * | 3/1993 | Eichmiller | 250/519.1 |
| 5,417,225 A | * | 5/1995 | Rubenstein et al. | 250/519.1 |
| 5,981,964 A | * | 11/1999 | McAuley et al. | 250/515.1 |

FOREIGN PATENT DOCUMENTS

| | | | | |
|---|---|---|---|---|
| DE | 3326880 A1 | * | 2/1985 | G21F/3/00 |

* cited by examiner

*Primary Examiner*—Jack I. Berman
(74) *Attorney, Agent, or Firm*—June E. Rickey; Calfee, Halter & Griswold LLP

(57) ABSTRACT

A radiation shield is provided for use on patients undergoing radiotherapy treatment. The shield is made of a suitable radiation absorbing material for preventing the transmission of high energy radiation to the patient's non-treatment areas. The device may further comprise an exterior surface layer for absorbing low energy photons. The shield is sized and shaped to conform to a patient's anatomy and to provide the necessary amount of absorbing material closest to the beam edge while not interfering with the beam. The shield may further comprise an optional cavity located on the interior surface of the shield which may be lined with a soft compressible material for conforming to a patient's unique anatomy. The shield may be further provided with dosimeters mounted on the exterior surface of the leading edge as well as on the interior surface of the shield. The dosimeters may be connected in a systematic manner with the linear accelerator such that the machine could be automatically switched off or warnings given if the patient is receiving too much radiation scatter dose.

21 Claims, 4 Drawing Sheets

RADIATION SHIELD

This application claims the benefit of Provisional application Ser. No. 60/136,987, filed Jun. 1, 1999.

FIELD OF THE INVENTION

The present invention pertains generally to a radiation detecting and shielding device for reducing radiation exposure to healthy tissue of a patient undergoing radiation therapy, as well as detecting the amount of radiation delivered to the patient. More particularly, the invention pertains to protecting the contra-lateral breast or chest wall of a patient undergoing radiotherapy as well as sensing the amount of radiation on or near a patient's skin on the non-treated side of the body.

BACKGROUND OF THE INVENTION

Radiation therapy or radiotherapy for the chest wall or breast area of a patient has been utilized frequently for the treatment of localized cancer such as breast cancer. A patient typically undergoes a series of radiation treatments in which the treatment area is irradiated with a high energy radiation dose on the order of 25 to 75 Gray (Gy.) units, with a typical treatment dose in the range of 50 to 60 Gy. The most common radiation therapy technique for treating breast cancer utilizes opposing tangential radiation beams. A pair of wedges are often used in conjunction with this technique to obtain a more uniform treatment dose.

It is a growing concern among researchers that patients are exposed to scattered radiation in the adjacent region of the radiation field, particularly in the contralateral breast or chest wall in treatment of the breast or chest area. For patients undergoing breast cancer radiotherapy treatment, it has been estimated that the contra-lateral breast receives a scattered radiation dose between 5% to 13% of the prescribed treatment dose. Some patients may receive an even higher percentage of the dose depending on the patient's anatomy and the treatment angles utilized. Further, for patients treated with a conventional dose of 50 Gray using traditional tangential fields, the dose to the contra-lateral breast has been estimated to be on the order of 2.5–6.0 Gray at a central axis corresponding to approximately 5 centimeters over the mid-line. Although the effects of this dose of scattered radiation are not yet well understood, one study has suggested that women under 45 years of age who had been treated for breast cancer by radiation therapy had an increased risk by a factor of 1.5 of contralateral breast cancer as compared to controls.

Radiotherapy to the breast region poses an increased exposure to scattered radiation dose compared to other sites of the body due to the wedge angles, beam accessories, and position of the linear accelerator gantry and collimator used for treatment. One source of scattered radiation is wedge scatter which results from the radiation beam scattered from the wedges used to shape the beam's energy. A second source of scattered radiation is caused by the collimator head leakage and scattered radiation from the primary collimators. A third source of scattered radiation is due to the internal scattering of the treatment beam in various directions within the patient's body.

It is generally considered prudent practice to reduce a patient's exposure to unnecessary scattered radiation if it is reasonable to do so. Prior art shielding devices have generally been developed to protect patients against low energy radiation such as that generated by typical x-rays and the like. These prior art devices have generally comprised a thin flexible layer of shielding material such as lead, which is sandwiched between fabric and which is generally worn and supported by the patient. One major disadvantage to these type of devices is that they are not effective for shielding patients from high energy radiation which is typically used in breast cancer treatment and tumor reduction. Another disadvantage to this type of device is that the design of the shield is not conducive to alteration, i.e., increasing the lead thickness to protect against high energy radiation since the lead would be too heavy and cumbersome for a patient to support. Third, these prior art devices are not conducive to being positioned in close proximity to the treatment area without interfering with the treatment beams from the collimator. Thus, because of these difficulties, it is currently accepted practice for patients undergoing breast radiotherapy to forgo the use of shields which reduce radiation exposure to non-treatment areas.

Radiotherapy treatment techniques have also been modified in order to reduce the radiation dose to the contra-lateral breast. One prior art technique is to substitute a thicker lateral wedge in place of the medial wedge. While this technique may reduce scattered radiation exposure to the contra-lateral breast, it may result in an undesirable non-homogeneous dose across the treatment region.

It is thus highly desirable to have a new and improved method and apparatus for substantially reducing the scattered radiation dose to the non-treatments areas of the patient undergoing high energy external radiotherapy such as that utilized in treating localized breast cancer. It is further desired to have a shielding device which is self-supporting and is easily manipulated into position without interfering with the treatment beam. In addition, it is desired to have a device which senses the radiation adjacent a patient's skin and whether the device is correctly positioned or is positioned in error too close to the treatment beam or target area. Thus, it is highly desirable to have an improved device and method which significantly reduces the prior art problems.

SUMMARY OF THE INVENTION

The present invention provides in one aspect a radiation shield for shielding a patient undergoing radiotherapy from scattered radiation, the shield comprising: a leading edge section having an inner surface complementary shaped to conform to a patient's anatomy, and said shield being comprised of a radiation absorbing material for absorbing high energy radiation.

The present invention provides in another aspect a radiation shield and support stand assembly for shielding a patient undergoing radiotherapy, the device comprising a shield made of radiation absorbing material for absorbing high energy radiation and a support stand for supporting said shield.

The present invention provides in yet another aspect a radiation shielding device for shielding a patient undergoing radiotherapy, the device comprising: a shield made of radiation absorbing material for absorbing high energy radiation with said plate having an external layer of material for absorbing low energy electrons.

The present invention provides in still another aspect a radiation shield for shielding the contralateral breast of a patient, the shield comprising a leading edge section having an exterior surface shaped such that a distal edge of said shield may be placed in close proximity with the midplane of a patient with said exterior surface being parallel and located in close proximity to said radiotherapy beams.

These and other aspects of the invention are herein described in particularized detail with reference to the accompanying Figures.

DETAILED DESCRIPTION OF THE FIGURES

Figure 5A:
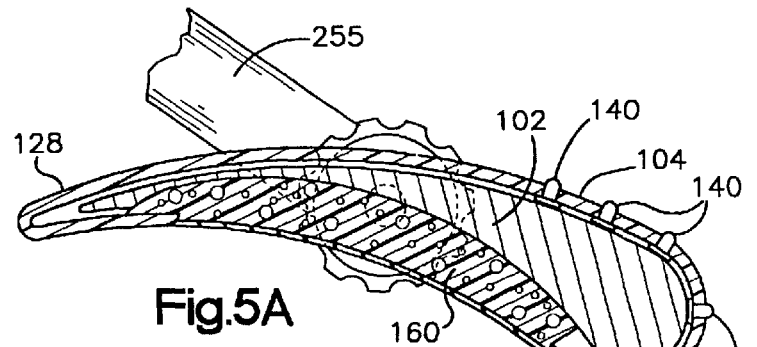
Figure 5B:
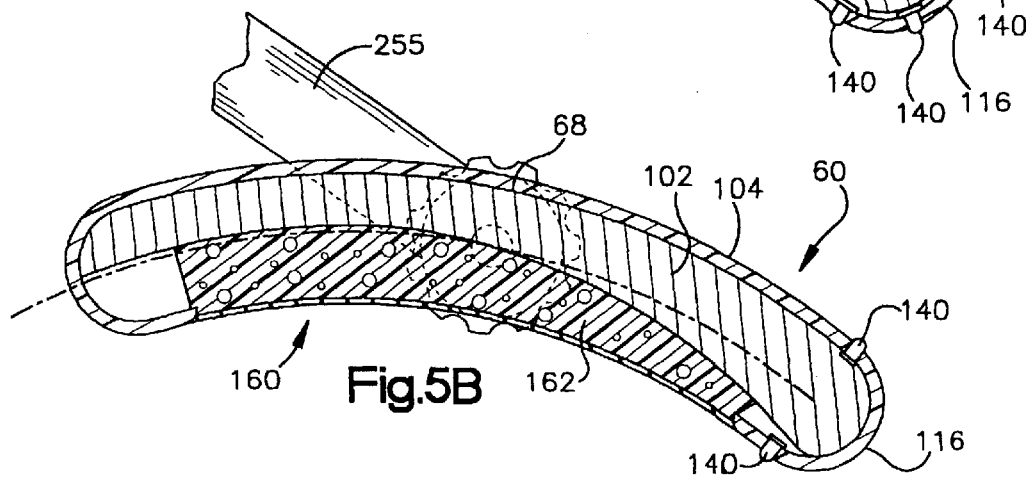
Figure 6:
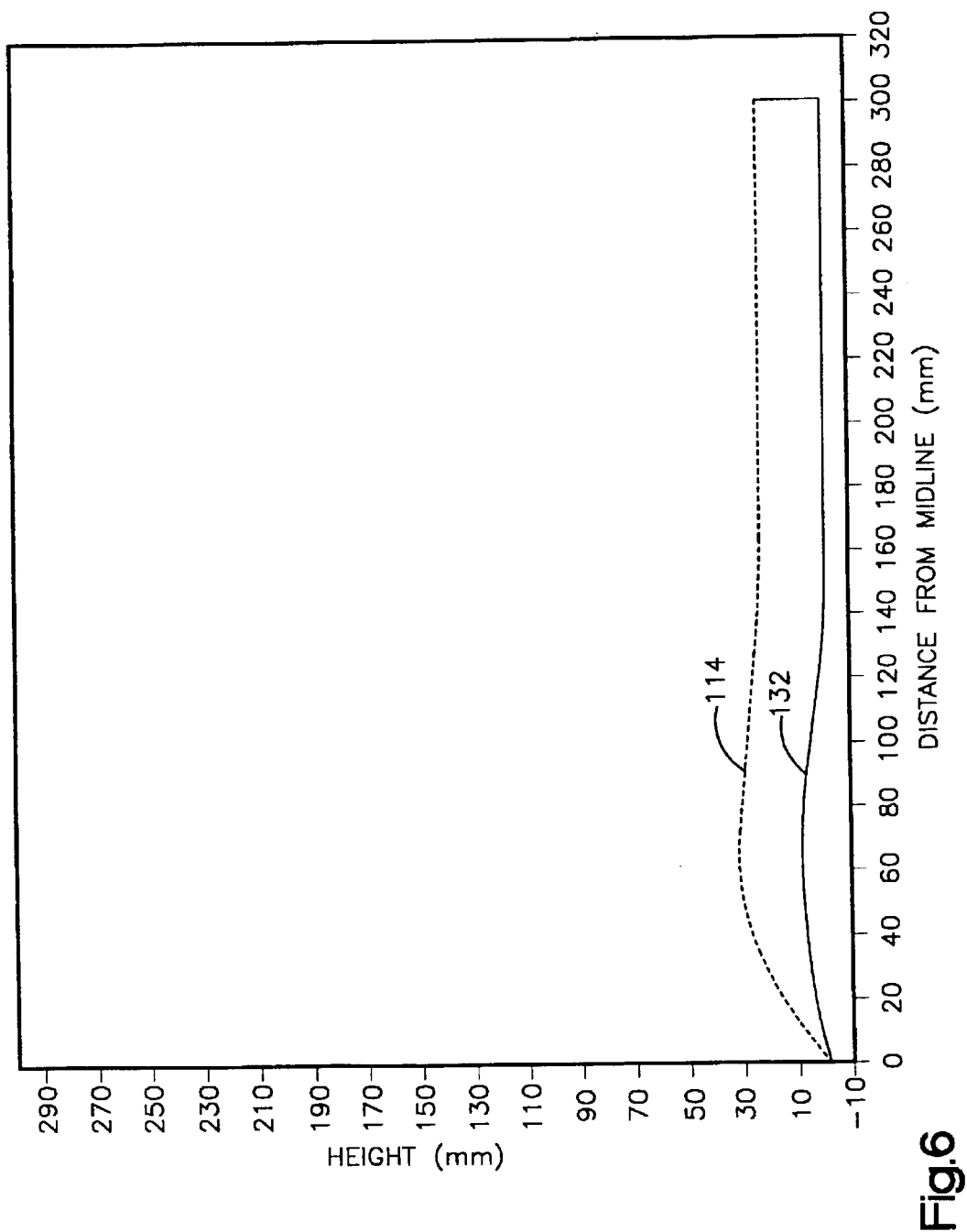

FIGS. 5a and 5b are cross-sectional views of alternate embodiments of the inventions shown with an optional interior cavity filled with a soft compressible material; and FIG. 6 illustrates the cross-sectional profile of a first embodiment of the shield 100 shown in relationship with the estimated breast curvature 132 of 95% of the female population.

DETAILED DESCRIPTION OF PREFERRED AND ALTERNATE EMBODIMENTS

Figure 1:
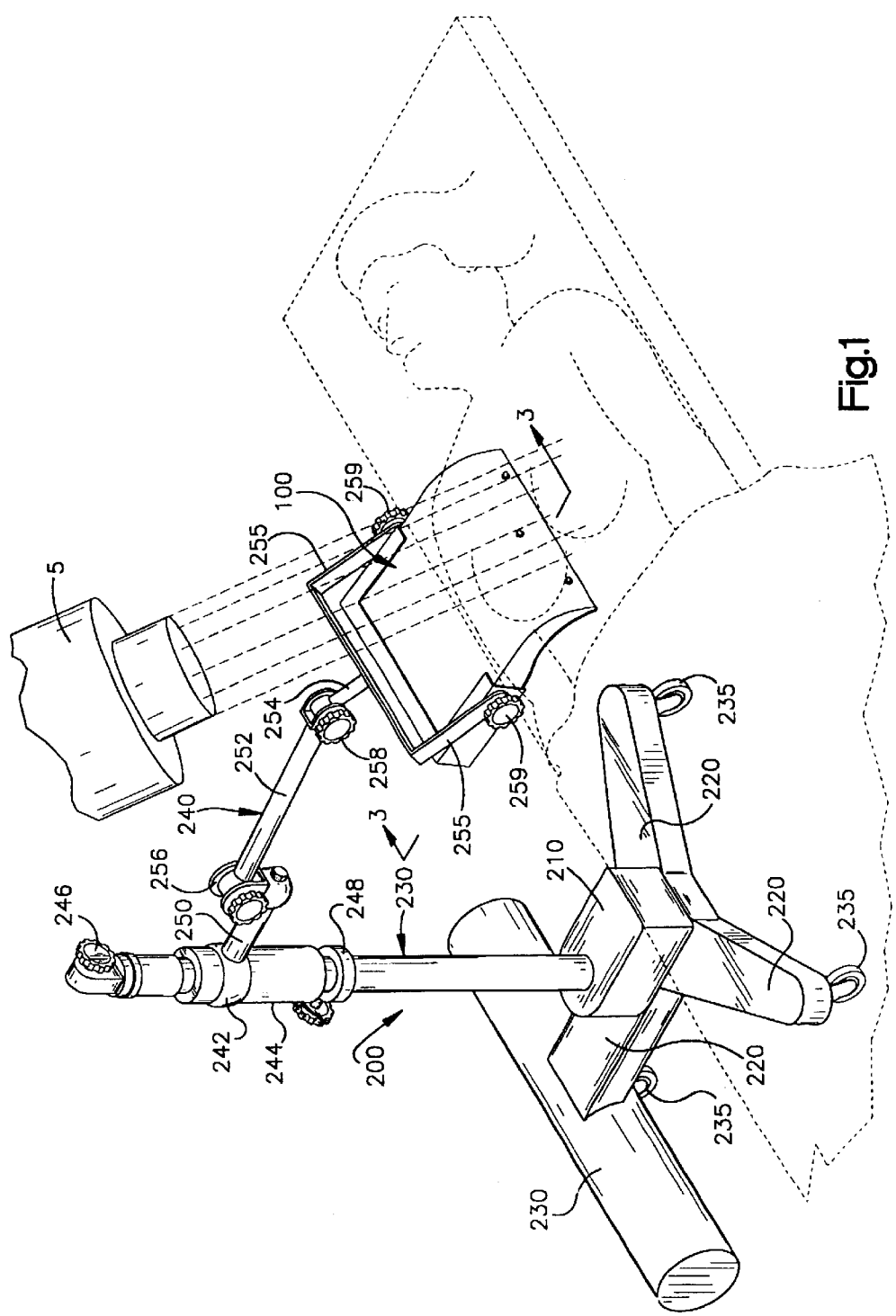
FIG. 1 is a perspective view of a adjustable radiation shield device and stand assembly of the present invention.

Turning to the drawings and particularly FIG. 1, there is shown a schematic of a female patient (shown in phantom) undergoing localized radiotherapy from a radiation source such as a collimator 5. A first embodiment of a radiation shield 100 of the invention is illustrated in use with an optional support stand assembly 200. As shown in phantom, tangential radiotherapy beams 72 originating from a collimator 5 are shown targeting the treatment region of the patient. The shield device 100 is shown shielding the patient's contralateral chest region from the scattered radiation of the radiotherapy beams 72 and collimator 5. However, the shield 100 may be sized and shaped to shield other patient areas such as the thyroid, testes, ovaries and the brain.

Figure 2:
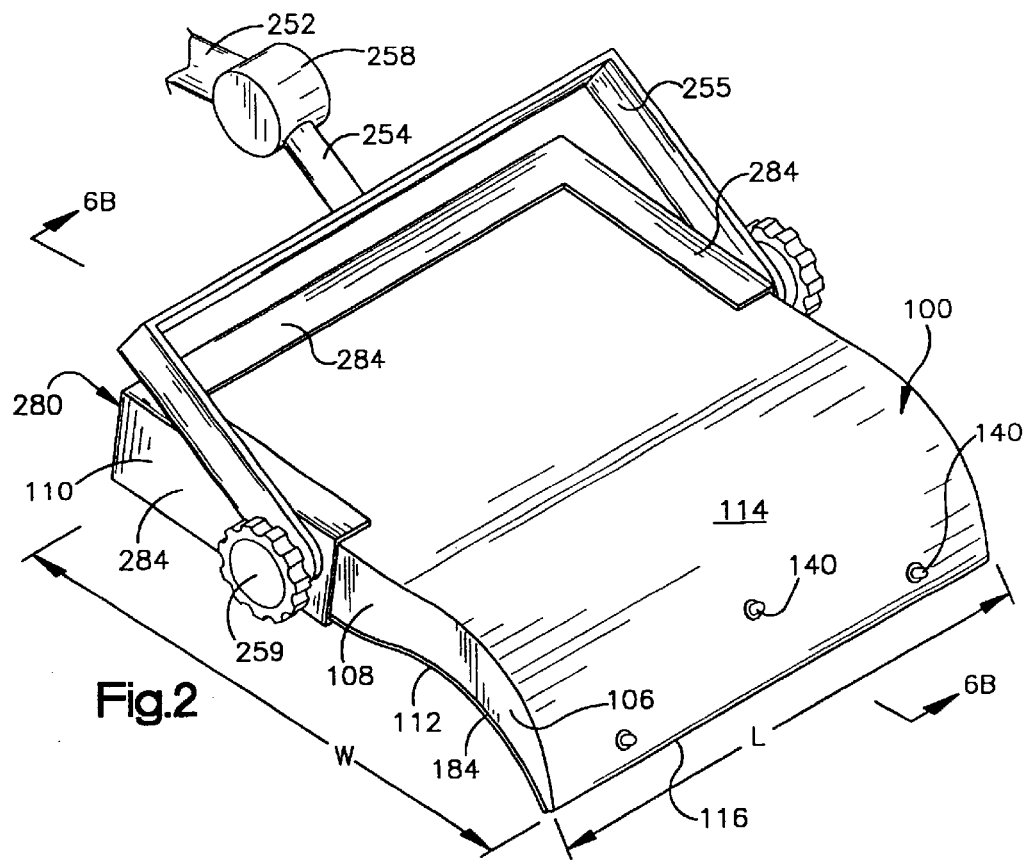
FIG. 2 is an enlarged perspective view of the adjustable radiation shield device as shown in FIG. 1.

As shown in FIG. 2, the shield 100 of a first embodiment of the invention comprises a rectangular plate preferably shaped to conform to a patient's anatomy and which is dimensioned to have a sufficient length L and width W to shield the adjacent region of the treatment area of the patient undergoing radiotherapy. For example, where the shield 100 is utilized to shield the contralateral breast of a female patient, the width W of the shield 100 is generally in the range of about 15 to about 30 centimeters, with a preferred range of about 20 to about 25 centimeters. Further, the length L of the shield 100 is generally in the range of about 15 to about 40 centimeters, with a preferred range of about 30 to about 35 centimeters. However, other dimensions of the shield may be utilized in order to tailor the shield to other anatomical sites such as the male testicular region.

The shield 100 is primarily comprised of a radiation absorbing material or any non-radioactive material having a high atomic number such as, but not limited to, lead, gold, tungsten, depleted uranium, or cerabend. Preferably, the shield material is lead. The shield 100 has an optional exterior surface layer 104 which is comprised of any suitable material such as rubber, polymeric, acrylic or other soft compressible material. Preferably, the exterior surface layer is comprised of polystyrene or other suitable material capable of absorbing low energy photons electrons. Preferably, the exterior surface layer has a minimum thickness in the range of about 0.10 to about 10 centimeters, and is vacuum molded or glued to the exterior surface of the radiation absorbing material 102.

Figure 3:
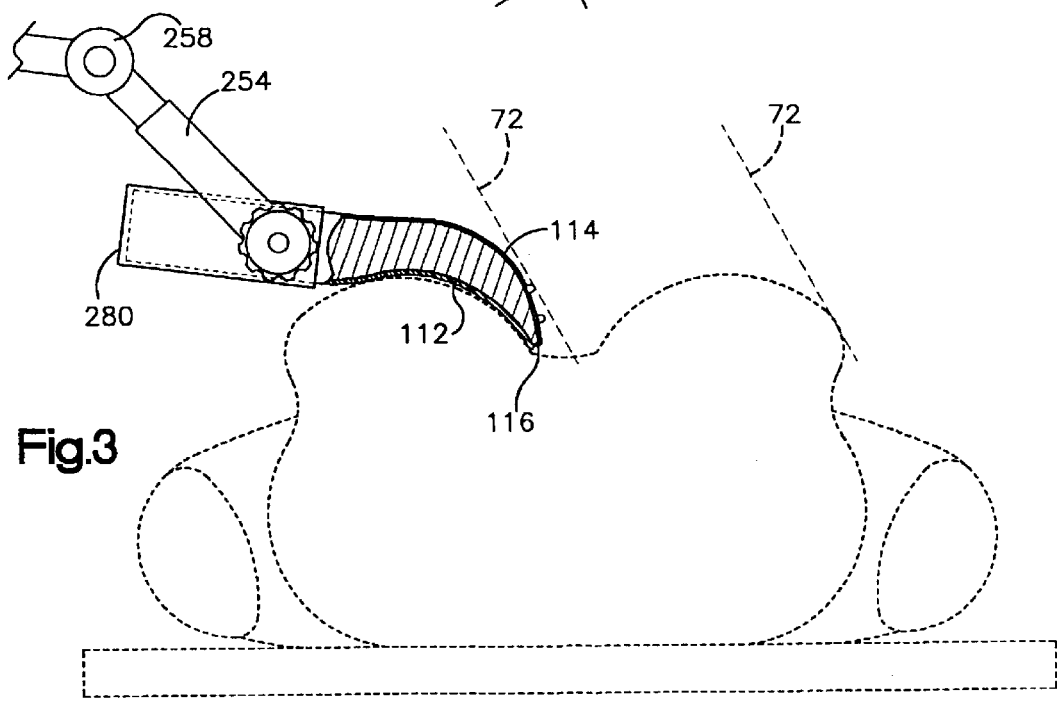
FIG. 3 is a cross-sectional view of the invention shown in use on a patient in the direction 3—3 as shown in FIG. 1.
Figure 4:
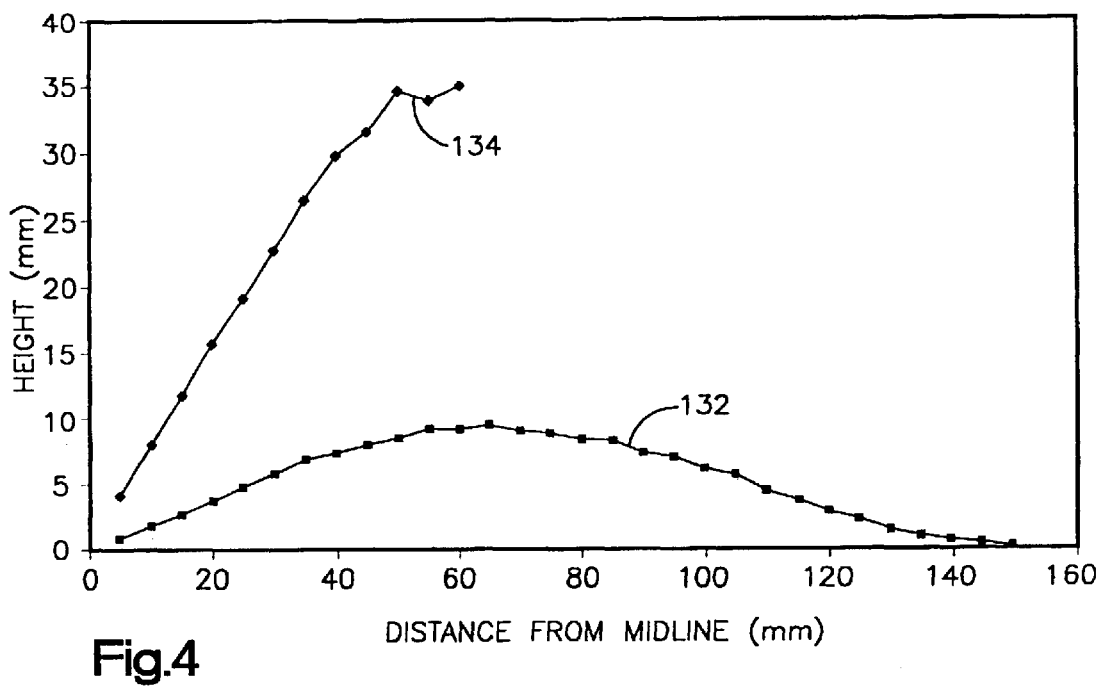
FIG. 4 illustrates the breast curvature 132 of 95% of the female population versus distance from the patient's midline; and the maximum height of the exterior surface of the shield 100 versus distance from the patient's midline.

The shield 100 further comprises a front or leading edge section 106, a mid section 108, and a rear section 110. The leading edge section 106 is preferably shaped such that the inner surface 112 of the shield 100 is capable of being placed in close proximity to the patient's skin, and preferably shaped to conform to the curvature of the anatomy of the site which is being shielded. For example as shown in FIG. 3, the curvature of the inner surface 112 of the shield 100 has been designed to match the breast curvature 132 of 95% of the female population as shown in FIG. 4. The estimated curvature 132 of the female population was determined experimentally by averaging the measurements of the breast curvature of a random selection of fifty female patients. It is further desired that the leading edge section 106 have smooth rounded edges in order to facilitate placement of the shield 100 in close proximity to the patient's skin.

The upper surface 114 of the leading edge section 106 is additionally shaped such that the exterior edge 116 of the leading edge section 106 may be placed in close proximity to the medial tangential field 72 (i.e., tangential radiation treatment beam) without interfering with the path of the radiation beam. This positioning of the shield 100 is especially desirable since the region of the patient nearest to the beam receives the highest scattered radiation exposure. As shown in FIG. 3, this may be accomplished by shaping or angling the upper surface 114 of the leading edge section 106 such that the surface 114 is approximately parallel or tangent to the radiotherapy beam 72. Thus, the treatment or gantry angle of the radiotherapy treatment field has been taken into consideration in the design of the leading edge 106 of the shield 100.

It is important that the leading edge section 106 of the shield 100 have a sufficient thickness of the radiation absorbing material 102 in order to protect the patient, yet be thin enough to be positioned as close as possible to the treatment area without interfering with the treatment beam. The preferred thickness of the leading edge 106 of the shield 100 was determined by experimentally measuring the average clearance distances of 50 patients undergoing radiotherapy treatment for breast cancer. The clearance distance is defined as the perpendicular distance between the medial tangential treatment field and the patient's skin as measured along the contra-lateral surface of each patient. Thus, it is preferred that the leading edge be tapered such that the thickness of the radiation absorbing material tapers from the mid-section 110 to the distal end or edge 116 of the leading edge section 108 such that the thickness of the shield does not exceed the corresponding clearance distances. Thus as further shown in FIG. 4, curve 134 illustrates the height (i.e., the summation of the clearance and breast curvature data) of the leading edge of the shield 100 in relationship to the breast curvature 132 of the patient. The allowable thickness of the shield 100 is the difference between these two curves. The leading edge section 106 preferably has a thickness in the range of about 2.0 to about 4.0 centimeters. It is more preferable that the leading edge thickness be in the range of about 2.0 to about 3.0 centimeters.

This tapered edge design 114 allows the shield 100 to be placed as close as possible to the medial treatment field without interfering with the treatment beam 72. For example as shown in FIG. 6, the leading edge of the shield may be designed to vary in thickness from 0.0 cm at the medial field border of the patient to approximately 3.0 cm at a distance of 4.0 cm from the medial field border based on the clearance measurements. This leading edge design results in a scattered radiation reduction of at least 90% at 1.0 cm from the medial field border. After 4.0 cm from the medial field border, there are no constraints on the thickness and the shield was designed as a constant thickness of 2.0 cm extending out to 30 cm, which would reduce the externally scattered radiation by at least 95%.

As shown in FIGS. 5a and 5b, the shield 100 may additionally comprise other cross-sectional shapes such as, but not limited to, a wing or symmetrically curved plate. For a wing cross-sectional shape as shown in FIG. 5a, the thickness of the shield tapers from the leading edge 116 to the trailing edge 128. At the leading edge section 106, the minimum radiation absorbing material thickness is in the range of about 2.0 to about 4.0 centimeters. Preferably, the leading edge radiation absorbing material thickness is in the range of about 2.0 to about 3.0 centimeters. This shaping feature of the invention significantly reduces the weight of the shield 100 since the radiation absorbing material is placed only where needed, so that the highest energy components of the scattered radiation are effectively attenuated by the thickest part of the shield.

As shown in FIG. 5b, the shield may also comprise a curved plate preferably having a curved shape to conform to the anatomy of the patient's area to be protected. The curved plate further preferably has smooth rounded edges.

All of the above described embodiments of the shield may further comprise a cutout section or cavity 160 located in the mid-section 108 of the shield 100 on the interior surface 112 which lies adjacent the patient's skin in order to facilitate placement of the shield in closer proximity to the tangential beam 72. This cavity 160 may further be lined with a layer of soft compressible material 162 such as foam or a gel pack which can conform to the patient's shape or contour as well as provide an increased level of comfort to the patient.

The embodiments of the shield 100 may be further provided with a plurality of dosimeters or radiation sensing devices 140 mounted on the exterior surface 114 of the shield 100 preferably on the leading edge section 106, as well as along the interior surface 112 of the shield. The dosimeters may preferably be of a thermoluminescent-type such as Model Number TLD-100 manufactured by Bicron, Inc. The dosimeters 140 mounted on the interior surface 112 are utilized to estimate the amount of radiation dose which is transmitted through the shield 100 near the patient's skin. These internally mounted dosimeters 140 may preferably be connected in a systematic manner with the collimator 5 such that the machine could be automatically switched off if the patient's radiation dose exceeds a predetermined level. Alternatively, the interior mounted dosimeters 140 may be connected to an enunciator panel and readout display panel to give warnings to medical personnel if the patient is receiving a radiation dose above or below predetermined levels. The internally mounted dosimeters could also be used to track the patient's cumulative dose over the treatment period.

Further, the exterior mounted dosimeters 140 may also be connected to a display panel to alert medical personnel when the measured radiation level exceeds a predetermined level in order to indicate that the shield 100 is improperly located within the radiation treatment field. Thus both the externally and internally mounted dosimeters 140 may facilitate placement of the shield 100 on the patient and allow for positional adjustments should the patient be receiving too much scattered radiation dose to the contralateral area or if the shield is misplaced within the treatment area.

The shield device 100 may further optionally comprise a support stand assembly 200. The support stand assembly 200 is supported by a conventional base 210 having three or more legs 220, with one of the legs 220 further comprising a counterweight 230, which has a weight sufficient to counterbalance the cantilevered shield 100. It is preferred that each of the support stand legs 220 have wheels 235 mounted thereon for easy mobility of the entire assembly 10. The base 220 or wheels 235 may further contain locking or braking means to maintain the desired positioning of the assembly 200. Extending up from the base 220 is a support column 230 from which a cantilevered support arm 240 extends therefrom.

The shield 100 is mounted upon the distal end of the support arm 240. A first end 242 of the support arm 240 is rotatably mounted upon the support column 230 for yaw adjustment of the arm 240 and the shield 100 thereon. The first end 242 of the support arm 240 is also disposed between a sliding sleeve 244 connected to a conventional pulley and counterweight system (not shown) which may be located within the interior of the hollow column 230. By rotating crank 246, the sliding sleeve 244 may be raised or lowered in order to adjust the vertical height of the support arm 240. Locking means 248 such as a retaining ring are provided in order to act as a safety stop to ensure the support arm 240 is secured in its desired vertical position should the pulley system fail.

The support arm 240 further comprises a first linkage 250, a second linkage 252, and a third linkage 254. Although three linkages are shown and described, one or more linkages may be utilized. A ball and socket type joint 256 or other rotary joint connects the first linkage 250 and the second linkage 252 such that pitch, yaw and roll adjustments of the shield 100 are provided. The support arm 240 further comprises a pitch adjusting joint 258 connecting the second and third linkage 252,254, for adjusting the pitch or angle of the shield 100 with respect to the second linkage 252. Thus placement of the shield may be facilitated by the pitch, yaw and roll adjustments as well as the vertical height adjustment. The optional stand assembly 200 is not limited to the above description, as any counterweighted stand capable of pitch and vertical adjustments of a cantilevered arm may be utilized. It is preferred that the stand have wheels as well as yaw and roll adjustment capability of the shield 100.

As shown in FIG. 2, the shield 100 may be mounted within a support structure 280 comprising a lower support plate 282 having sides 284 shaped to form a channel or frame for receiving the shield 100 therein. The support structure is preferably made of a strong material such as steel. The shield 100 and support frame 280 further comprise aligned holes (not shown) for receiving a steel rod 290 therein. The shield 100 and support frame 280 are rotatably mounted between the forked distal ends 255 of the third linkage 254 of the support arm 240 to further facilitate placement upon the patient. The threaded shanks of locking knobs 259 are inserted into aligned holes of the forked distal ends 255 and the shield 100 for locking the shield 100 into its desired rotary position. Preferably, the shield 100 is rotatably mounted about, or very close to, its center of gravity.

Although the invention has been disclosed and described with respect to certain preferred embodiments, certain variations and modifications may occur to those skilled in the art upon reading this specification. For example other cross-sectional shapes of the shield could be utilized. Any such variations and modifications are within the purview of the invention notwithstanding the defining limitations of the accompanying claims and equivalents thereof.

We claim:

1. A radiation shield for shielding a patient undergoing radiotherapy from scattered radiation, the shield comprising:

a leading edge section having an inner surface complementary shaped to conform to a patient's anatomy, and said shield being comprised of a radiation absorbing material for absorbing high energy radiation, wherein the thickness of said leading, edge section tapers from a mid section to a distal edge.

2. The shield of claim 1 wherein said shield further comprises an exterior surface shaped for being placed in close proximity to said radiotherapy beams without interfering with said beams.

3. The shield of claim 1 wherein said exterior surface is parallel to said radiotherapy beams.

4. The shielding device of claim 1 wherein said shield has an external layer of material for absorbing low energy electrons.

5. The shielding device of claim 4 wherein said external layer is made of material selected from the group of polystyrene, polymeric, rubber or acrylic.

6. The shielding device of claim 4 wherein said external layer has a thickness in the range of about 0.1 to about 10 centimeters.

7. The shield of claim 1 wherein said leading edge section is shaped for being placed approximately tangent to said radiotherapy beam.

8. The shielding device of claim 1 wherein said leading edge has a thickness in the range of about 2 to about 4 centimeters.

9. The shielding device of claim 1 wherein said radiation absorbing material is selected from the group comprising: lead, gold, cerabend or depeleted uranium.

10. The shield of claim 1 wherein said interior surface has a cavity lined with a soft conformable material for conforming to a patient's shape.

11. The shield of claim 1 wherein said shield is supported by a stand assembly.

12. The assembly of claim 11 wherein said stand assembly further comprises a base having a counterweight.

13. The assembly of claim 12 wherein said stand assembly further comprises a support column extending up from said base and having a support arm slidably mounted to said support column for raising or lowering said shield mounted upon said support arm.

14. The assembly of claim 12 wherein said base has a plurality of wheels mounted thereon.

15. The assembly of claim 12 wherein said stand assembly further comprises a support arm having said shield mounted thereon, with said support arm comprising one or more joints for adjusting the pitch of said shield.

16. The assembly of claim 15 wherein said support arm comprises one or more joints for adjusting the roll of said shield.

17. The assembly of claim 15 wherein said support arm comprises one or more joints for adjusting the yaw of said shield.

18. The shield of claim 1 wherein an exterior surface of said shield is angled downwardly in the range of 20–60 degrees from the horizontal direction.

19. A radiation shield for shielding a patient undergoing radiotherapy from scattered radiation, the shield comprising: a leading edge section having an inner surface complementary shaped to conform to a patient's anatomy, and said shield being comprised of a radiation absorbing material for absorbing high energy radiation, wherein said shield has a cross-sectional shape of an airfoil.

20. A radiation shield for shielding a patient undergoing radiotherapy from scattered radiation, the shield comprising: a leading edge section having an inner surface complementary shaped to conform to a patient's anatomy, and said shield being comprised of a radiation absorbing material for absorbing high energy radiation, wherein said interior surface has one or more means for sensing radiation.

21. A radiation shielding device for shielding a patient undergoing radiotherapy, the device comprising: a shield made of radiation absorbing material for absorbing high energy radiation with said device having an external layer of material for absorbing low energy electrons, wherein one or more dosimeters are mounted upon said external layer of said shield.

* * * * *